United States Patent [19]

Drehman et al.

[11] 4,053,533
[45] Oct. 11, 1977

[54] OXIDATION OF ACETYLENIC IMPURITIES WITH COPPER MANGANITE CATALYST

[75] Inventors: Lewis E. Drehman; Floyd Farha, Jr.; Arlo J. Moffat, all of Bartlesville, Okla.

[73] Assignee: Phillips Petroleum Company, Bartlesville, Okla.

[21] Appl. No.: 622,591

[22] Filed: Oct. 15, 1975

[51] Int. Cl.$^2$ .......................... C07C 7/01; B01J 23/34; B01J 23/84
[52] U.S. Cl. .......................... 260/681.5 R; 252/471; 260/674 R; 260/676 R; 260/677 A
[58] Field of Search .................. 260/681.5 R, 681.5 C, 260/677 A, 674 R, 676 R; 252/471, 476

[56] References Cited

U.S. PATENT DOCUMENTS

| | | | |
|---|---|---|---|
| 1,971,168 | 8/1934 | Weiss | 252/471 X |
| 2,381,707 | 8/1945 | Wood et al. | 260/677 A |
| 2,408,970 | 10/1946 | Doumani et al. | 260/681.5 R |
| 2,426,604 | 9/1947 | Frevel | 260/681.5 R |
| 3,202,727 | 8/1965 | Dancer | 260/681.5 R |
| 3,327,013 | 6/1967 | Frevel et al. | 260/681.5 R |
| 3,549,719 | 12/1970 | Duyvermen et al. | 260/677 A |
| 3,634,536 | 1/1972 | Frevel et al. | 260/681.5 R |
| 3,663,457 | 5/1972 | Tamura et al. | 252/471 X |
| 3,897,511 | 7/1975 | Frevel et al. | 260/681.5 R |
| 3,922,318 | 11/1975 | Martino et al. | 260/681.5 R |

FOREIGN PATENT DOCUMENTS

| | | | |
|---|---|---|---|
| 193,664 | 5/1967 | U.S.S.R. | 260/677 A |

OTHER PUBLICATIONS

Bowen et al., Jour. Soc. Chem. Ind., vol. 69, No. 3, pp. 65-69, (1950).

*Primary Examiner*—Daniel E. Wyman
*Assistant Examiner*—Thomas A. Waltz

[57] ABSTRACT

Acetylenic compounds are selectively removed from hydrocarbon mixtures containing same by oxidation in the presence of a solid copper-manganese-oxygen catalyst. In one embodiment, acetylenic compounds are selectively removed from a conjugated diene mixture containing same by contacting oxygen and a mixture with a copper manganite catalyst under oxidizing conditions.

7 Claims, No Drawings

OXIDATION OF ACETYLENIC IMPURITIES WITH COPPER MANGANITE CATALYST

This invention relates to the purification of unsaturated hydrocarbon-containing mixtures to remove undesirable contaminants therefrom. In accordance with one aspect, this invention relates to a method of removing unsaturants such as acetylenes from hydrocarbon mixtures containing same by contacting the mixture and oxygen at an elevated temperature with a copper-manganese-oxygen catalyst. In accordance with a further aspect, this invention relates to a process for the purification of conjugated diene-containing mixtures also containing acetylenic compounds as impurities by contacting at an elevated temperature with a copper manganite catalyst under oxidation conditions. In accordance with a further aspect, this invention relates to a process for the purification of the effluent from an oxidative dehydrogenation process by oxidizing the effluent with a copper manganite catalyst to selectively remove acetylenic compounds therefrom.

The present invention provides a method whereby acetylenes such as vinylacetylenes, methylacetylene, 1-butyne, and the like can be selectively removed from hydrocarbon mixtures containing same, especially conjugated diene mixtures containing them, without the necessity for hydrogenation and extensive fractionation. There is thus provided a means whereby substantial reduction in plant investment and utility is realized.

The invention relates more specifically to a process for removing acetylenic compounds (impurities) found in small amounts, i.e., 0.5–1 mol percent, in refinery streams comprising paraffins, olefins, diolefins, water, nitrogen, oxygen, etc. The product gas stream obtained by the vapor phase catalytic oxidation of butenes to form butadiene is a typical stream which can be treated by the process of the present invention. Such a gas stream contains, in addition to butadiene, unreacted butenes, water, oxygen, nitrogen, carbon dioxide, carbon monoxide, and traces of acetylene. The presence of acetylene in the product is most undesirable, causing difficulties in the subsequent separation of butadiene from unreacted butenes and being an unacceptable impuritiy in the final product.

It has now been found that by selective oxidation in the presence of a solid manganese-copper-oxygen catalyst it is possible to remove the acetylenes from such gaseous streams without loss of butadiene by oxidation.

Accordingly, an object of this invention is to provide a simplified process for removing acetylenes from unsaturated hydrocarbon-containing mixtures such as conjugated diene streams.

Another object of this invention is to provide an improved process for removing acetylenes from conjugated diene-containing mixtures to provide a highly purified conjugated diene-containing stream.

A further object of this invention is to provide a process for purification of conjugated diene streams obtained from oxidative dehydrogenation processes whereby acetylenic contaminants are removed therefrom.

Other objects, aspects, and the several advantages of this invention will be apparent to those skilled in the art upon a study of the disclosure and the appended claims.

According to the present invention, a process for the removal by selective oxidation of acetylenic compounds from a gas stream containing same is provided which comprises passing the gas stream in admixture with sufficient oxygen over a solid copper-manganese-oxygen catalyst under conditions of temperature and pressure sufficient to remove a substantial portion of the acetylenes present without destroying desirable unsaturated hydrocarbons present in the stream treated.

More specifically, according to this invention, acetylenic compounds in hydrocarbon-containing streams such as butadiene-containing streams are removed by selective oxidation under reaction conditions in the presence of free oxygen by contact with a copper manganite catalyst.

The solid catalysts utilized in the process of this invention consist of copper, manganese, and oxygen in which the atomic ratio of copper to manganese can vary from about 0.25:1 to about 4:1. Particularly useful compositions have empirical formulas such as $Cu_3Mn_2O_6$, $Cu_2Mn_2O_5$, $CuMnO_2$, $CuMn_2O_3$, $CuMn_3O_4$, and $CuMn_2O_4$, and mixtures thereof. The catalysts are prepared by employing conventional techniques including intimate mixing of the oxides or hydroxides by ball milling, grinding, and the like, and by coprecipitation of the oxalates or hydroxides from a solution containing dissolved salts of the metals. The precipitate is washed to remove soluble contaminants such as, for example, potassium nitrate, sodium chloride, sodium sulfate, and the like. The purified material is then dried and calcined in air for about 30 minutes to 20 hours or longer at temperatures ranging from about 500° to 1600° F (260°–871° C), more preferably from about 900°–1100° F (482°–593° C).

Small amounts of such metals as iron, magnesium, silicon, and calcium can be present in the finished catalyst, as well as lesser amounts of chromium, aluminum, and nickel in the form of oxides, silicates, etc., providing the total amount of such metals does not exceed about five weight percent. Generally, the amounts of aluminum and nickel will be no more than about 0.01 weight percent each, chromium will be no more than about 0.1 weight percent, and the remainder will be no more than about 1 weight percent each.

U.S. Pat. No. 3,365,337 describes the formation of copper manganites by coprecipitation of an aqueous solution of copper sulfate and manganese sulfate with a solution of sodium hydroxide. The resulting mixed hydroxides are washed, and the purified mixture is then calcined in air at about 1100° F (593° C). The calcined product had an empirical formula of $CuMn_2O_4$.

Metal oxides that can be used in forming the catalysts include cupric oxide, cuprous oxide, manganous oxide, manganic oxide, manganous manganic oxide ($Mn_3O_4$), and manganese dioxide. Metal salts of copper and manganese that can be employed in formulating the aqueous solutions include the acetates, chlorides, formates, nitrates, sulfates, etc. The finished (calcined) catalyst has an apparent bulk density of about 1 gram per cc and a surface area ranging from about 8–50 square meters per gram. In the process of the invention, the calcined catalyst is utilized in the form of particles ranging in size from about 4 to 40 mesh, more preferably from about 8 to 20 mesh. If desired, the powdered catalyst can also be formed into pellets, wafers, etc., ranging in size from about 1/32 to ¼ inch or more by utilizing conventional pelleting practices.

As indicated above, it is desirable to remove the acetylenes prior to separating the various hydrocarbons associated in such refinery streams since they may form gums, etc., thus complicating the separation process. It is also desirable that butadiene, isoprene, etc., isolated from such streams contain very little acetylenes, i.e., less than about 100 ppm and preferably less than about 50 ppm when the diolefin is to be polymerized in a solution process with a stereospecific catalyst. The acetylenes slow the polymerization rate unless compensated by the use of additional catalyst and may adversely affect the quality of the elastomer or resin produced because some relatively low molecular weight material may be formed.

The process of the present invention can be carried out under a wide range of oxidation conditions, depending upon feedstock, catalysts, the desired degree of acetylene removal, and the desired type of operation. Reaction can be carried out in any suitable apparatus and can be carried out batchwise or continuously. Continuous operation through a fixed catalyst bed is presently preferred. However, other modes of reaction can be used.

The process conditions suitable in practicing this invention include reaction temperatures ranging from about 250°–800° F (121°–427° C), more preferably from about 400°–650° F (204°–343° C); reaction pressure ranging from about 0.5–500 psig (3.4–3447 kPag), more preferably from about 5–100 psig (34–689 kPag); an oxygen to hydrocarbon mol ratio ranging from about 0.01–0.2, more preferably about 0.02–0.12; and a steam to hydrocarbon mol ratio of 0 to 100, more preferably 0 to 50. Hydrocarbon feed rates can range from about 50 to about 5000 gaseous hourly space velocity (GHSV).

The catalysts utilized in the process of the present invention are active and relatively long-lived. However, they do become less active with the passage of time, and when this occurs they can be regenerated at process temperatures by shutting off the feed and passing air over the catalyst bed.

EXAMPLE

Invention catalyst A was a catalyst comprising about 27 weight percent copper, about 41 weight percent manganese, less than 4 weight percent of a mixture of metals previously described, and the balance combined oxygen (obtained commercially) and corresponding approximately to the empirical formula $CuMn_2O_4$. The ground material was calcined in air for 4 hours at 900° F (482° C), cooled, and sieved to condition it for use in the oxidation process. The particles ranging in size from 18–40 mesh were retained for use. The calculated copper content was 26.8 weight percent.

Control catalyst B was an intimate mixture of cupric oxide and alumina with a calculated copper content of 30.8 weight percent. It was prepared by mixing 110 g cupric oxide powder with a slurry of 175 g of alumina powder in water for 10 minutes in an Osterizer blender. The mixture was dried, calcined in air for 8 hours at 500° C (932° F), cooled, ground, and sieved. The particles ranging in size from 18–40 mesh were retained for use. Copper aluminate may have been formed in view of the calcining temperature.

A hydrocarbon-containing steam comprising butadiene, butenes, oxygen, nitrogen, carbon dioxide, carbon monoxide, and traces of vinylacetylene was contacted under oxidation conditions with both invention catalyst A and control catalyst B. In each run, three cc (except Run 1 which used 10 cc) of the catalyst was charged to a tubular, fixed bed reactor. The conditions employed and the results obtained are presented in Tables I and II.

TABLE I

Oxidation of Vinylacetylene over $CuMn_2O_4$ Catalyst

| Run No. | Catalyst Age, Hrs. | Temp., °F (°C) | Pressure, psig (kPa) | Feed, GHSV* | Oxygen/Feed Mol Ratio | Steam/Feed Mol Ratio | % CONVERSION Vinyl-acetylene | Buta-diene | Bu-tenes |
|---|---|---|---|---|---|---|---|---|---|
| 1 | 29 | 450 (232) | 10 (68.9) | 905 | 0.02 | 0 | 100 | 0.3 | −0.3 |
| 2 | 38 | 450 (232) | 10 (68.9) | 926 | 0.03 | 0 | 100 | 1.1 | −7.9 |
| 3 | 57 | 450 (232) | 10 (68.9) | 627 | 0.03 | 0 | 100 | 1.5 | −13.8 |
| 4 | 68 | 450 (232) | 10 (68.9) | 2102 | 0.03 | 0 | 100 | 0.1 | 0.3 |
| 5 | 87 | 450 (232) | 10 (68.9) | 1871 | 0.03 | 0 | 100 | 0.5 | −2.9 |
| 6 | 187 | 550 (288) | 11 (75.8) | 1060 | 0.03 | 0 | 100 | 1.7 | −13.1 |
| 7 | 218 | 550 (288) | 10 (68.9) | 910 | 0.04 | 22 | 100 | 0.4 | 6.4 |
| 8 | 314 | 550 (288) | 10 (68.9) | 970 | 0.04 | 20 | 100 | 1.6 | −1.9 |
| 9 | 319 | 550 (288) | 10 (68.9) | 2000 | 0.03 | 20 | 100 | 1.1 | −2.7 |
| 10 | 321 | 550 (288) | 15 (103) | 4020 | 0.03 | 18 | 84.5 | 0.9 | −4.4 |
| 11 | 340 | 550 (288) | 10 (68.9) | 720 | 0.11 | 23 | 100 | 0.9 | 6.0 |
| 12 | 395 | 550 (288) | 10 (68.9) | 730 | 0.04 | 31 | 100 | 2.4 | −4.8 |
| 13 | 419 | 550 (288) | 33 (227) | 1370 | 0.17 | 22 | 61.6 | 3.4 | −1.8 |
| 14 | 422 | 600 (315) | 32 (221) | 1320 | 0.17 | 26 | 66.5 | 5.4 | −2.9 |
| 15 | 427 | 550 (288) | 10 (68.9) | 1670 | 0.03 | 11 | 100 | 3.4 | −14.7 |
| 16 | 451 | 550 (288) | 10 (68.9) | 1890 | 0.01 | 11 | 100 | 0.7 | −4.1 |

*GHSV = Gaseous hourly space velocity.
NOTE:
Typical feed composition, mole %, effluent from Run 4 as example of products obtained.

| | Feed | Effluent | | Feed | Effluent |
|---|---|---|---|---|---|
| Oxygen | 2.56 | 0.25 | cis-2-Butene | 4.88 | 4.81 |
| Nitrogen | 9.14 | 9.25 | Butadiene | 79.38 | 80.23 |
| Carbon monoxide | 0.00 | 0.05 | Vinylacetylene | 0.134 | 0.000 |
| Carbon dioxide | 0.00 | 1.33 | | | |
| Propane | 0.01 | 0.01 | | | |
| Propylene | 0.01 | 0.01 | | | |
| n-Butane | 0.23 | 0.08 | | | |
| neo-Pentane | 0.17 | 0.18 | | | |
| 1-Butene | 1.30 | 1.34 | | | |
| trans-2-Butene | 2.36 | 2.46 | | | |

Inspection of the results in Table I reveals that the invention catalyst is operable for extended periods in the absence or presence of steam as a diluent. Runs 1–6 show the catalyst oxidized 100 percent of the vinylacetylene at temperatures ranging from 450°–550° F in the absence of steam with only 0.3 to 1.7 percent of the butadiene being oxidized at the same time and an oxygen/feed mol ratio of about 0.03. The catalyst age was 187 hours and it was still performing well. Steam was then introduced. After lining out, the catalyst performed in a similar manner at 550° F, an oxygen/feed mol ratio ranging from about 0.01 to 0.11 and a steam/- feed mol ratio ranging from about 11/1 to about 23/1. (Increasing the steam/feed mol ratio to 31/1 also increased the amount of butadiene converted to 2.4 percent, however.) Also, when the oxygen/feed ratio was increased to 0.17, the efficiency of the catalyst declined somewhat since conversion of acetylene amounted to about 62 percent (Run 13). Increasing the temperature to 600° F increased acetylene conversion to about 66 percent (Run 14). Under these conditions, a combination of perhaps insufficient oxygen and/or a decreased contact time due to the increased volume of reactants passing the catalyst per unit time was predominating and 100 percent conversion of acetylene was not achieved. However, 10 percent acetylene conversion was again obtained by restoring the oxygen/feed ratio to about 0.03 (Run 15), although more than 3 percent of the butadiene was also being destroyed. However, in a few more hours (Run 16), the catalyst had resumed converting 100 percent of the acetylene while converting less than 1 percent of the butadiene and thus it had attained its original good activity. The test was terminated after 451 hours.

TABLE II

Oxidation of Vinylacetylene over CuO . Al$_2$O$_3$ Catalyst

| Run No. | Catalyst Age, Hrs. | Temp., °F (°C) | Feed, GHSV** | Oxygen/Feed Mol Ratio | Steam/Feed Mol Ratio | % CONVERSION | | |
|---|---|---|---|---|---|---|---|---|
| | | | | | | Vinyl-acetylene | Buta-diene | Butenes |
| 1 | 5.9 | 400 (204) | 1010 | 0.03 | 0 | 95 | 0.3 | 4.5 |
| 2 | 6.9 | 500 (260) | 1000 | 0.03 | 0 | 100 | 0.6 | 3.9 |
| 3 | 21.1 | 500 (260) | 1120 | 0.03 | 0 | 100 | 0.3 | 5.0 |
| 4 | 36.7 | 500 (260) | 1125 | 0.03 | 0 | 15.5 | −0.5 | 4.9 |
| 5 | 39.5* | 500 (260) | 865 | 0.04 | 0 | 13.4 | 0.6 | 1.1 |
| 6 | 44 | 500 (260) | 1045 | 0.04 | 0 | 100 | 1.3 | 3.4 |
| 7 | 47.9 | 400 (204) | 785 | 0.04 | 28 | 28.5 | 0.5 | 1.4 |
| 8 | 48.9 | 500 (260) | 715 | 0.05 | 42 | 92.1 | 1.0 | 0.8 |
| 9 | 49.6 | 600 (315) | 600 | 0.05 | 37 | 100 | 1.8 | 0.8 |
| 10 | 53.4 | 600 (315) | 640 | 0.06 | 32 | 100 | 1.0 | 5.3 |
| 11 | 68.7 | 600 (315) | 575 | 0.07 | 37 | 100 | 1.2 | 5.7 |

*Regenerated.
**Gaseous hourly space velocity.

The control catalyst is also capable of oxidizing 100 percent of the acetylene as the data presented in Table II show. However, it required regeneration between 21 and 37 hours (Runs 1-4) to restore its effectiveness whereas the invention catalyst was still 100 percent effective. Not enough data were collected over an extended period to compare both catalysts in the presence of steam. Since the control catalyst was performing well after about 20 hours in a steam environment, it is possible it was copper aluminate which could be expected to have steam stability rather than a mixture of copper oxide and alumina. Alumina deteriorates in a steam atmosphere.

We claim:
1. A process for the selective removal of acetylenic contaminants or impurities present in hydrocarbon streams which comprises contacting oxygen and a hydrocarbon-containing mixture contaminated with acetylenic compounds with a catalyst consisting essentially of copper, manganese, and oxygen in which the atomic ratio of copper to manganese varies from about 0.25:1 to about 4:1 under oxidation conditions including a temperature and a mol ratio of oxygen to hydrocarbon sufficient to selectively remove a substantial portion of said acetylenic compounds present in said mixture.

2. A process according to claim 1 wherein said contacting is effected at a temperature ranging from about 250°-800° F, a reaction pressure ranging from 0.5-500 psig, an oxygen to hydrocarbon mol ratio ranging from 0.01-0.2, and a steam to hydrocarbon mol ratio of 0-100.

3. A process according to claim 1 wherein the mixture comprises butadiene.

4. A process according to claim 1 wherein said contacting is effected in the presence of oxygen and steam at a temperature in the range of about 400°-650° F.

5. A process according to claim 1 wherein said mixture is a butadiene mixture obtained as the effluent from the oxidative dehydrogenation of olefins and the effluent contains oxygen, steam, and 1-acetylenes, as well as butadiene, and the contacting is effected at a temperature in the range of about 400°-650° F.

6. A process according to claim 1 wherein the catalyst is at least one composition having the formula Cu$_3$Mn$_2$O$_6$, Cu$_2$Mn$_2$O$_5$, CuMnO$_2$, CuMn$_2$O$_3$, CuMn$_3$O$_4$, and CuMn$_2$O$_4$.

7. A process according to claim 1 wherein said catalyst is CuMn$_2$O$_4$.

* * * * *